United States Patent

Höllinger et al.

[11] 3,960,960
[45] June 1, 1976

[54] 1,1-DIPHENYL-1-LOWER ALKOXY-AMINO-ALKANES AND THE SALTS THEREOF

[75] Inventors: Roderich Höllinger, Leonding near Linz; Wolf Wendtlandt, Linz; Gerda Schneider, Linz, Dornach, all of Austria

[73] Assignee: Chemie Linz Aktiengesellschaft, Linz, Austria

[22] Filed: July 10, 1975

[21] Appl. No.: 594,673

Related U.S. Application Data

[63] Continuation-in-part of Ser. No. 395,447, Sept. 10, 1973, abandoned.

[30] Foreign Application Priority Data

Sept. 11, 1972 Austria .................. 7764/72

[52] U.S. Cl. ............... 260/570 R; 260/501.12; 260/501.17; 260/501.18; 260/562 B; 260/562 P; 260/566 F; 424/316; 424/330
[51] Int. Cl.$^2$ .................................... C07C 93/00
[58] Field of Search ...... 260/570 R, 501.12, 501.17, 260/501.18

[56] References Cited
UNITED STATES PATENTS

| | | | |
|---|---|---|---|
| 3,384,662 | 5/1968 | Höllinger et al. | 260/570 |
| 3,395,146 | 7/1968 | Safzinger | 260/570 X |
| 3,441,602 | 4/1969 | Höllinger et al. | 260/501.12 |

*Primary Examiner*—Robert V. Hines
*Attorney, Agent, or Firm*—Wenderoth, Lind & Ponack

[57] ABSTRACT

Basic ethers having the general formula:

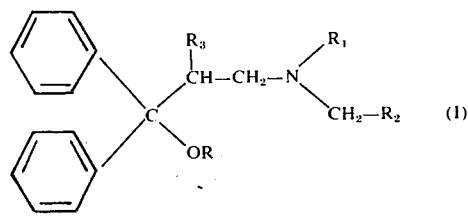

in which R is lower alkyl, $R_1$ is hydrogen, lower alkyl, allyl or benzyl, $R_2$ is alkenyl, aralkenyl, optionally substituted by alkoxy, haloalkenyl, alkinyl, cycloalkyl or cycloalkylidenemethyl and $R_3$ is hydrogen or methyl and their salts, which compounds have good analgesic and morphineantagonistic action.

8 Claims, No Drawings

1,1-DIPHENYL-1-LOWER ALKOXY-AMINO-ALKANES AND THE SALTS THEREOF

This application is a continuation in part to our co-pending application Ser. No. 395,447 of Sept. 10, 1973 and now abandoned.

This invention relates to basic ethers and the preparation thereof. The invention is also concerned with pharmaceutical compositions containing such basic ethers in admixture with diluents.

In accordance with the invention there is provided a basic ether having the general formula:

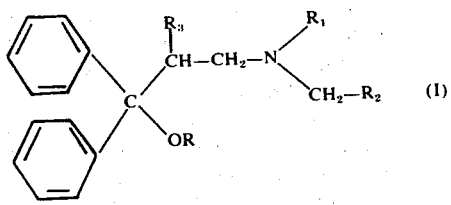

in which R is an alkyl group containing up to four carbon atoms, $R_1$ is a hydrogen atom, a lower alkyl group containing up to four carbon atoms, an allyl group or a benzyl group, $R_2$ is an alkenyl group containing up to six carbon atoms, an aralkenyl group, or an aralkenyl group substituted by a lower alkoxy group, with the alkenyl group containing up to four carbon atoms, a halogenoalkenyl group containing up to six carbon atoms, an alkinyl group containing up to three carbon atoms, a cycloalkyl group containing up to six carbon atoms or a cycloalkylidenemethyl group containing up to seven carbon atoms and $R_3$ is a hydrogen atom or a methyl group, and salts thereof.

In particular the invention provides compounds of the formula I, in which $R_1$ is a hydrogen atom, a lower alkyl group containing up to four carbon atoms or a benzyl group, $R_2$ is an alkenyl group containing up to six carbon atoms, an aralkenyl group or an aralkenyl group substituted by a lower alkoxy group, with the alkenyl group containing up to four carbon atoms, an alkinyl group containing up to three carbon atoms, a cycloalkyl group containing up to six carbon atoms or a cycloalkylidenemethyl group containing up to seven carbon atoms and R and $R_3$ are as defined in formula I and the pharmaceutically acid addition salts thereof.

More specific, compounds of formula I are preferred in which $R_1$ is hydrogen or a lower alkyl group containing up to four carbon atoms, $R_2$ is akenyl containing up to six carbon atoms and cycloalkyl containing up to six carbon atoms, R and $R_3$ are as defined in formula I and the pharmaceutically acid addition salts thereof. Amongst this, the compounds 1,1-diphenyl-1-methoxy-3-allylamino-propane, 1,1-diphenyl-1-ethoxy-3-methallylamino-propane, 1,1-diphenyl-1-ethoxy-3-allylamino-propane, 1,1-diphenyl-1-methoxy-3-(cyclopropylmethyl)-amino-propane and 1,1-diphenyl-1-methoxy-3-methyl-allylamino-propane and the pharmaceutically acceptable acid addition salts thereof can be mentioned.

The compounds according to the invention are substances having a good analgesic and, at the same time, morphine-antagonistic action.

It is known that morphine and other strong narcotic analgesics, when used regularly, cause addiction which leads to physical and psychological dependence on the drug and greatly limits the therapeutic use of these substances. Compounds having morphine-antagonistic properties are capable of counteracting the effects of morphine and hence causing withdrawal symptoms in animals addicted to morphine. Since the compounds according to the invention, in addition to possessing the morphine-antagonistic action, also possess an analgesic action, they may be used as analgesics, and because of their properties being opposed to the action of morphine it may be concluded from the general opinions held, that they do not cause addiction.

Prior to the present invention, numerous compounds having morphine-antagonistic properties have been disclosed, and some of these also possess a simultaneous analgesic action. However, the disclosed compounds are complicated heterocyclic compounds, that is to say compounds which possess the nitrogen atom as a basic center built into a ring. In contrast, the compounds according to the present invention have the simple structure of an aliphatic amine.

Furthermore, prior compounds have been prepared which possess the structure of the above general formula (I) but in which the groups bonded to the nitrogen atom do not contain an unsaturated group and do not contain any cycloalkyl groups. Such compounds are described in US-patent applications Ser. No. 535,715 and Ser. No. 536,313 of two of the inventors, now US-patent Nos. 3,441,602 and 3,384,662. Admittedly, some of these prior compounds also possess an analgesic action, but they lack the morphine-antagonistic properties possessed by compounds according to the invention which ensure their harmlessness with regard to causing addiction.

The present invention also provides a process for the preparation of a conpound of formula (I), which comprises reacting a compound having the general formula:

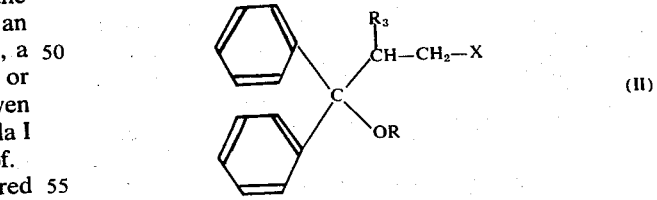

in which R and $R_3$ have the same meaning as given above with respect to formula (I) and X is

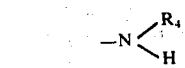

or $-N=CH-R_5$, wherein $R_4$ is a lower alkyl group, an allyl group, a benzyl group or an acyl group which may be split off hydrolytically and $R_5$ an a optionally substituted aryl group, with a halide having the general formula:

wherein Hal is a halogen atom and $R_2$ is as defined above with respect to formula (I), thereafter splitting off the $CH-R_5$ group or $R_4$ acyl group, present in the reaction product, by alkaline or acid treatment and optionally replacing the $R_1$ hydrogen atom by an alkyl or benzyl group or, if the group $-CH_2-R_2$ is an allyl group, by a further allyl group, and thereafter converting the resulting base into a salt or liberating the free base from the salt.

It is desirable to carry out the reaction in a suitable inert solvent and, in order to reduce the reaction time, at an elevated temperature. However, in principle, the conversion is achievable even at room termperature. Furthermore it has proved useful to add a suitable base, such as, for example, pyridine, triethylamine or sodium carbonate, in order to bind the hydrogen halide produced during the reaction. This avoids the starting amine itself acting as an acid acceptor and thus partially being withdrawn from the reaction.

If it is intended to prepare compounds of the general formula (I) in which $R_1$ is a hydrogen atom, the process is conducted with starting compounds of the forumla (II) which contain, in the amine part, an acyl group which may be split off by alkaline treatment. In such a case, the compound of fomuula (II) in which $R_4$ is a hydrolytically removable acyl group, is preferably converted into the alkali metal compound by treatment with an alkali metal hydride in an aprotic solvent, particularly of high polarity, and the alkali metal compound is subsequently reacted with the compound of formula (III). A preferred aprotic solvent is hexamethylphosphoric acid tris-amide. After reaction with the halogen compound of formula (III), the protective acyl group is subsequently split off by alkaline hydrolysis.

Protective groups which have proved particularly advantageous are groups of acids which contain an electron-attracting group such as, for example, the trifluoromethyl group, which may be split off particularly easily by alkaline treatment. In principle, however, other suitable acid groups also may be used.

The introduction of the protective group may be effected by reaction of the appropriate amine with an acid derivative such as, for example, a halide, anhydride or ester, at room temperature or elevated temperature and optionally in the presence of an agent which takes up hydrogen halide or in the presence of an esterification catalyst.

The hydrolytic splitting off of the protective group may be effected by treatment with an aqueous alkali, particularly at elevated temperature.

In the reaction of the halogen compound of formula (III) with the compound of formula (II) containing an acyl group, it is to be noted that this acylated amine is not basic and therefore in such a case, a base must be added as the acid acceptor. The addition of sodium hydride, preferably in excess, which does not have to be removed specially during the working up of the batch, has proved particularly advantageous for this purpose. The hydrolysis of the protective group may follow directly without purification of the intermediate product, by adding water to the reaction mixture.

However it is also possible, when preparing compounds of formula (I) in which $R_1$ is a hydrogen atom, to start from compounds of formula (II) in which the amine part of the molecule is converted into an azomethine with an aromatic aldehyde, for example benzaldehyde or a substituted benzaldehyde. This azomethine is reacted with the halogen compound of formula (III) to give a quaternary compound from which the aldehyde is subsequently split off again.

The azomethine is formed by reaction of the two reactants in a suitable solvent, such as, for example, an alcohol, preferably at an elevated temperature. In some cases it has proved advisable to remove the water formed in the reaction by distillation, and in such a case a solvent which is immiscible with water may serve as the entraining agent. The reaction with the halogen compound of formula (III) can be carried out in a suitable solvent, particularly at elevated temperature, but it is also possible for an excess of the halogen compound to serve as the diluent. The splitting off of the aldehyde may be effected very easily by means of dilute aqueous acid at room temperature. In such a case, the quaternary salt does not have to be isolated specially.

A variant of the process according to the invention for the manufacture of compounds of general formula (I), wherein $R_1$ is an alkyl or benzyl group, is first to prepare, according to one of the indicated methods, a compound of formula (I) in which $R_1$ is a hydrogen atom, and subsequently to introduce an alkyl or benzyl group into the amine group of this compound. The introduction of these groups may be carried out, for example, analogously to the introduction of the $-CH-R_2$ group. However it is also possible first to acylate the secondary amine by reaction with a halide, an anhydride or a reactive ester of a lower aliphatic carboxylic acid, of acrylic acid or of benzoic acid and to convert the acyl group into the $R_1$ group by reduction with a complex hydride of aluminium, for example lithium aluminium hydride or sodium dihydro-bis-(methoxyethoxy)-aluminate. The acylation may be carried out in the usual manner, for example in the presence of an acid acceptor when an acid chloride or anhydride is employed. In the case of the introduction of a methyl group, the introduction also may be effected in a simple manner in a single reaction step by means of a mixture of formic acid and formaldehyde.

If the compound is prepared in the form of the base, it may be converted into the corresponding salt by means of an appropriate acid, according to customary methods. Such a salt may be, for example: a hydrohalide, sulphate, tartrate, mandelate, fumarate or cyclohexylsulphamate. If the compound is obtained as a salt during working up, the free base may be isolated therefrom according to customary methods.

The primary and secondary amines which serve as the starting compounds for the process according to the invention are in part new and have in part been given by way of example in our earlier patent specifications. A list of these amines is set out after Example 8 herein.

The amines may be prepared by removing one or both benzyl groups from the N,N-dibenzyl compounds or N-alkyl-N-benzyl compounds by hydrogenation, using palladium as the catalysat (US-Patent Specification No. 3,384,662). The removal of the second benzyl group by hydrogenation is not described in this patent specification, but may be achieved at a higher temperature (60° to 80°C).

The N,N-dibenzyl compounds and N-alkyl-N-benzyl compounds themselves are obtainable, in the case when R₃ is hydrogen atom, according to the process described in US-Patent Specification No. 3,441,602. When R₃ is a methyl group, the compounds may be prepared according to the process described in Austrian Specification No. 270,617.

The secondary starting amines are also obtainable, in the case when R₃ is a hydrogen atom, according to Austrian Patent Specification No. 264,501.

The following Examples illustrate the present invention and the manner in which it may be performed.

EXAMPLE 1

5.4 g of 1,1-diphenyl-1-ethoxy-3-methylaminopropane, 3.4 g sodium carbonate, 2.9 g of allyl bromide and 70 ml of 95 % strength tetrahydrofuran are boiled for 2 hours. After distilling off the solvent, the residue is extracted with ether; after evaporation of the ether, 4.8 g (70 % of theory) of 1,1-diphenyl-1-ethoxy-3-methylallylaminopropane are left as a viscous oil. The hydrochloride is precipitated in ether by means of hydrogen chloride and has a melting point of 114° to 117°C after recrystallisation from ethyl acetate.

EXAMPLE 2

26.9 g. of 1,1-diphenyl-1-ethoxy-3-methylaminopropane, 16.0 g. of allyl bromide and 200 ml. of ether are mixed and left to stand for 20 hours at room temperature. The hydrobromide of the starting base, which has separated out, is then separated off. The filtrate, on evaporation, yields 13.4 g. of oily 1,1-diphenyl-1-ethoxy-3-methylallylaminopropane (39% of theory). The hyrochloride is precipitated therefrom as in Example 1 and has a melting point of 115° to 119°C.

55% of the starting base may be recovered from the above hydrobromide.

EXAMPLE 3

5.8 g. of 3,3-diphenyl-3-methoxy-propylamine, 7.0 g. of allyl bromide, 8.1 g. of sodium bicarbonate and 100 ml. of dimethylformamide are reacted as in Example 1. 7.7 g. (100% of theory) of oily 1,1-diphenyl-1-methoxy-3-diallylaminopropane are obtained and, after conversion into the hydrochloride as in Example 1, the product has a melting point of 143° to 145°C.

EXAMPLE 4 a. 12.0 g. of 3,3-diphenyl-3-methoxy-propylamine, 13.5 g. of trifluoroacetic anhydride, 6.0 g. of pyridine and 100 ml. of benzene are stirred for 1 hour at 40°C. The mixture is cooled to 0°C. and water is added. The organic layer is separated off, washed with dilute hydrochloric acid and water and evaporated. 16.5 g. of N-(3,3-diphenyl-3-methoxypropyl)-trifluoroacetamide of melting point 108° to 110°C. are obtained, corresponding to a yield of 98% of theory.

b. 8.0 g. of the above acid amine are dissolved in 80 ml. of hexamethylphosphoric acid tris-amide, 1.7 g. of sodium hydride are added and the mixture is stirred for 3 hours. 5.7 g. of allyl bromide are then added dropwise and the mixture is stirred for a further 30 minutes. Water is then added and the reaction product is extracted by shaking with benzene. The benzene solution is evaporated and the residue is boiled for one hour with 100 ml. of 75% strength ethanol and 1 g. of sodium hydroxide. The ethanol is distilled off and the reaction product is extracted with ether. 6.5 g. of 1,1-diphenyl-1-methoxy-3-allylaminopropane of melting point 40° to 50°C. are obtained, corresponding to a yield of 97% of theory.

The hydrochloride obtainable therefrom has a melting point of 136° to 137°C., then crystallises again and finally melts at 153°C.

The hydrobromide obtainable from the base melts at 134.5° to 135.5°C.

EXAMPLE 5

16.7 g. of N-(3,3-diphenyl-3-methoxypropyl)-trifluoroacetamide, prepared according to Example 4, and 24.2 g. of allyl bromide in 150 ml. of anhydrous acetone are heated to 50°C. and 11.2 g. of powdered potassium hydroxide are added. The mixture is then boiled for 5 minutes and the solvent is distilled off in vacuo. The residue is boiled for one hour with 100 ml. of water and 100 ml. of methanol and is worked up as in Example 4. 13.1 g. of 1,1-diphenyl-1-methoxy-3-allylaminopropane of melting point 45° to 50°C. are obtained, corresponding to a yield of 93% of theory.

EXAMPLE 6 a. 48.2 g. of 3,3-diphenyl-3-methoxy-propylamine and 21.2 g. of benzaldehyde in 150 ml. of alcohol are boiled for 1 Rour and cooled, and the crystals are filtered off. 63.3 g. of N-(3,3-diphenyl-3-methoxy-propyl) benzaldimine of melting point 137° to 141°C. are obtained, corresponding to a yield of 96% of theory.

b. 15 g. of the above azomethine are boiled for 36 hours with 150 ml. of allyl bromide and the excess allyl bromide is then distilled off. The residue is stirred for some time with 60 ml. of 0.5% strength hydrobromic acid and 250 ml. of ether. The oil which has separated out crystallises after some time and is separated off. 8.8 g. of 1,1-diphenyl-1-methoxy-3-allylaminopropane hydrobromide are obtained, corresponding to a yield of 53% of theory. After recrystallisation from water, the hydrobromide as a melting point of 134.5° to 135.5°C.

EXAMPLE 7 a. 2.8 g. of 1,1-diphenyl-1-methoxy-3-allylaminopropane, prepared according to Example 4, 1.5 g. of triethylamine and 1.1 g. of propionic acid chloride in 60 ml. of benzene are warmed to 40°C. for 1 hour. Water is then added and the layers are separated. The organic layer is washed with sodium carbonate solution and water and evaporated and the residue is recrystallised from cyclohexane. 3.3 g. of N-(3,3-diphenyl-3,3-diphenyl-3-methoxypropyl)-N-allylpropionic acid amide are obtained as a viscous oil; this corresponds to 98% of theory.

b. 1.5 g. of lithium aluminium hydride are suspended in 80 ml. of ether and a solution of 3.3 g. of the above acid amide in 30 ml. of ether is added dropwise whilst stirring. Thereafter the mixture is boiled for 6 hours. The excess of the reducing agent is decomposed by means of 7.5 ml. of water and the ether solution is separated from the inorganic salts and evaporated. Distillation of the evaporation residue at 150°C. and 0.4 mm. Hg gives 2.8 g. of 1,1-diphenyl-1-methoxy-3-propyl-allyl-aminopropane as a viscous oil, corresponding to a yield of 87% of theory. The hydrochloride manufactured therefrom has a melting point of 143° to 145°C.

EXAMPLE 8

5.0 g. of 1,1-diphenyl-1-methoxy-3-allylaminopropane, prepared according to Example 4, 5.5 ml. of aqueous 35% strength formaldehyde solution and 7.0 ml. of formic acid are boiled for one hour. The reaction mixture is then rendered alkaline with sodium hydroxide solution and is extracted by shaking with ether. After evaporating off the ether, a residue of 5.0 g. of 1,1-diphenyl-1-methoxy-3-allyl-methyl-amino-propane is left in the form of an oil, which corresponds to 95% of theory. The hydrochloride may be obtained by precipitation with hydrogen chloride in ether solution and has a melting point of 173° to 175°C. after recrystallisation from ethyl acetate.

The amines used as starting substances are in part new. They are once again listed below:

1,1-Diphenyl-1-methoxy-3-aminopropane (disclosed in Austrian Patent Specification No. 266,085). Base: Melting point 66° to 68°C.

1,1-Diphenyl-1-ethoxy-3-aminopropane (new). Base: Oily. Hydrochloride, melting point 195° to 197°C.

1,1-Diphenyl-1-propoxy-3-aminopropane (new). Base: Melting point 45° to 50°C., boiling point 122° to 125°C./0.02 mm. Hg.

1,1-Diphenyl-1-1-butoxy-3-aminopropane (new). Base: Melting point 50° to 54°C. Hydrochloride, melting point 130° to 135°C. 1,1-Diphenyl-1-methoxy-3-methylaminopropane (disclosed in Austrian Patent Specification No. 264,501).

1,1-Diphenyl-1-ethoxy-3-methylaminopropane (disclosed in Austrian Patent Specification No. 264,501).

1,1-Diphenyl-1-propoxy-3-methylaminopropane (disclosed in Austrian Patent Specification No. 264,501).

1,1-Diphenyl-1-methoxy-2-methyl-3-aminopropane (new). Base: Oily. Hydrochloride, melting point 150° to 155°C.

1,1-Diphenyl-1-ethoxy-2-methyl-3-aminopropane (new). Base: Oily. Hydrochloride, melting point 148° to 150°C.

1,1-Diphenyl-1-propoxy-2-methyl-3-aminopropane (new). Base: Oily. Hydrochloride, melting point 197° to 198°C.

1,1-Diphenyl-1-methoxy-2-methyl-3-methylaminopropane (new). Base: Oily. Hydrochloride: Amorphous.

1,1-Diphenyl-1-ethoxy-2-methyl-3-methylaminopropane (new). Base: Oily. Hydrochloride hydrate, melting point 85°C.

1,1-Diphenyl-1-methoxy-3-benzylaminopropane (disclosed in Austrian Patent Specifications Nos. 264,501, 255,401 and 266,085).

1,1-Diphenyl-1-ethoxy-3-benzylaminopropane (disclosed in Austrian Patent Specification No. 264,501).

Primary amines are manufactured by removing 2 benzyl radicals by hydrogenation.

Analogously to Examples 1 to 8, it is possible to prepare, for example, the compounds listed in the tabulation which follows.

1,1-Diphenyl-1-ethoxy-3-allylaminopropane hydrobromide hydrate, melting point 81° to 87°C.

1,1-Diphenyl-1-propoxy-3-allylaminopropane hydrochloride, melting point 164° to 167°C.

1,1-Diphenyl-1-propoxy-3-allyl-methylaminopropanehydrochloride, melting point 125° to 128°C.

1,1-Diphenyl-1-methoxy-3-crotylaminopropane hydrochloride, melting point 178° to 180°C.

1,1-Diphenyl-1-ethoxy-3-crotylaminopropane hydrochloride, melting point 182° to 185°C.

1,1-Diphenyl-1-ethoxy-3-crotyl-methylaminopropane hydrochloride, melting point 133° to 135°C.

1,1-Diphenyl-1-methoxy-3-($\beta$-methallyl)-aminopropane mandelate, melting point 160°C.

1,1-Diphenyl-1-methoxy-3-($\beta$-methallyl)-methylaminopropane hydrochloride, melting point 169° to 173°C.

1,1-Diphenyl-1-ethoxy-3-($\beta$-methallyl)-methylaminopropane hydrochloride, melting point 99° to 103°C.

1,1-Diphenyl-1-methoxy-3-($\gamma,\gamma$-dimethylallyl)-aminopropane hydrochloride, melting point 138° to 140°C.; recrystallised from water melting point 85° to 88°C.

1,1-Diphenyl-1-ethoxy-3-($\gamma,\gamma$-dimethylallyl)-aminopropane hydrochloride, melting point 183° to 184.5°C.

1,1-Diphenyl-1-propoxy-3-($\gamma,\gamma$-dimethylallyl)-aminopropane hydrochloride, melting point 156° to 159°C.

1,1-Diphenyl-1-propoxy-3-($\gamma,\gamma$-dimethylallyl)-methylaminopropane hydrogen-fumarate, melting point 130° to 135°C.

1,1-Diphenyl-1-methoxy-3-cinnamylaminopropane hydrochloride, melting point 195° to 198°C.

1,1-Diphenyl-1-ethoxy-3-cinnamylaminopropane hydrochloride, melting point 214° to 218°C.

1,1-Diphenyl-1-methoxy-3-cinnamyl-methyl-aminopropane hydrochloride, melting point 183° to 188°C.

1,1-Diphenyl-1-propoxy-3-cinnamyl-methyl-aminopropane hydrochloride, melting point 168° to 173°C.

1,1-Diphenyl-1-methoxy-3-(p-methoxy-cinnamyl)-aminopropane hydrochloride, melting point 166° to 169°C.

1,1-Diphenyl-1-ethoxy-3-(trans-$\gamma$-chloroallyl)-methylaminopropane hydrochloride, melting point 118° to 125°C.

1,1-Diphenyl-1-ethoxy-3-($\beta$-chloroallyl)-amino-propane mandelate, melting point 134° to 137°C.

1,1-Diphenyl-1-methoxy-3-($\beta$-bromoallyl)-aminopropane hydrochloride, melting point 168° to 172°C.

1,1-Diphenyl-1-methoxy-3-($\beta$-bromoallyl)-methylaminopropane hydrochloride, melting point 183° to 186°C.

1,1-Diphenyl-1-methoxy-3-($\beta$-cyclohexylidene-ethyl)-aminopropane hydrochloride, melting point 193° to 195°C.

1,1-Diphenyl-1-ethoxy-3-($\beta$-cyclohexylidene-ethyl)-aminopropane hydrochloride, melting point 203° to 206°C.

1,1-Diphenyl-1-methoxy-3-propargylaminopropane hydrochloride, melting point 161° to 163°C.

1,1-Diphenyl-1-ethoxy-3-propargylaminopropane hydrochloride, melting point 168° to 172°C.

1,1-Diphenyl-1-methoxy-3-propargyl-methylaminopropane hydrochloride, melting point 182° to 185°C.

1,1-Diphenyl-1-methoxy-3-(cyclopropylmethyl)-aminopropane hydrochloride, melting point 179° to 180°C.

1,1-Diphenyl-1-ethoxy-3-(cyclopropylmethyl)-aminopropane hydrochloride, melting point 179° to 181°C.

1,1-Diphenyl-1-propoxy-3-(cyclopropylmethyl)-aminopropane hydrochloride, melting point 170° to 174°C.

1,1-Diphenyl-1-methoxy-3-(cyclopropylmethyl)-methylaminopropane hydrochloride, melting point 168° to 169°C.

1,1-Diphenyl-1-ethoxy-3-(cyclopropylmethyl)-methylaminopropane hydrochloride, melting point 154.5°C. to 156°C.

1,1-Diphenyl-1-propoxy-3-(cyclopropylmethyl)-methylaminopropane hydrochloride, as an amorphous powder.

1,1-Diphenyl-1-methoxy-3-(cyclobutylmethyl)-aminopropane hydrochloride, melting point 194° to 196°C.

1,1-Diphenyl-1-ethoxy-3-(cyclobutylmethyl)-methylaminopropane hydrochloride, melting point 129° to 130°C.

1,1-Diphenyl-1-methoxy-2-methyl-3-allylaminopropane hydrochloride, melting point 125° to 128°C.

1,1-Diphenyl-1-ethoxy-2-methyl-3-allylaminopropane mandelate, melting point 152° to 155°C.

1,1-Diphenyl-1-propoxy-2-methyl-3-allylaminopropane mandelate, melting point 147° to 149°C.

1,1-Diphenyl-1-methoxy-2-methyl-3-crotylaminopropane hydrochloride hydrate, melting point 78° to 85°C.

1,1-Diphenyl-1-ethoxy-2-methyl-3-crotylaminopropane mandelate, melting point 108° to 110°C.

1,1-Diphenyl-1-methoxy-2-methyl-3-($\gamma,\gamma$-dimethylallyl)-aminopropane hydrochloride, melting point 128° to 130°C.

1,1-Diphenyl-1-ethoxy-2-methyl-3-($\gamma,\gamma$-dimethylallyl)-aminopropane hydrochloride, melting point 137° to 139°C.

1,1-Diphenyl-1-propoxy-2-methyl-3-($\gamma,\gamma$-dimethylallyl)-aminopropane mandelate, melting point 129° to 131°C.

1,1-Diphenyl-1-methoxy-2-methyl-3-diallylaminopropane hydrochloride, melting point 160° to 161°C.

1,1-Diphenyl-1-ethoxy-2-methyl-3-($\beta$-cyclohexylideneethyl)-aminopropane mandelate, melting point 138° to 142°C.

1,1-Diphenyl-1-methoxy-2-methyl-3-cinnamyl-aminopropane mandelate, melting point 166° to 169°C.

1,1-Diphenyl-1-methoxy-2-methyl-3-(cyclobutylmethyl)-aminopropane hydrochloride, melting point 198° to 200°C.

1,1-Diphenyl-1-methoxy-2-methyl-3-($\beta$-bromoallyl)-aminopropane hydrochloride, melting point 148° to 150°C.

1,1-Diphenyl-1-methoxy-2-methyl-3-allyl-methylaminopropane hydrochloride, melting point 102° to 110°C.

1,1-Diphenyl-1-ethoxy-2-methyl-3-allyl-methyl-aminopropane hydrochloride, melting point 152° to 155°C.

1,1-Diphenyl-1-methoxy-2-methyl-3-($\gamma,\gamma$-dimethylallyl)-methylaminopropane hydrochloride, melting point 165° to 168°C.

1,1-Diphenyl-1-methoxy-2-methyl-3-crotyl-methyl-aminopropane hydrochloride, melting point 135° to 138°C.

1,1-Diphenyl-1-methoxy-2-methyl-3-($\beta$-bromoallyl)-methylaminopropane hydrochloride hydrate, melting point 103° to 110°C.

1,1-Diphenyl-1-methoxy-2-methyl-3-($\beta$-methallyl)-methylaminopropane hydrochloride, melting point 171° to 177°C.

1,1-Diphenyl-1-methoxy-2-methyl-3-($\gamma$-trans-chloroallyl)-methylaminopropane hydrochloride hydrate, melting point 100° to 105°C.

1,1-Diphenyl-1-methoxy-2-methyl-3-($\beta$-chloroallyl)-methylaminopropane hydrochloride hydrate, melting point 85° to 100°C.

1,1-Diphenyl-1-methoxy-2-methyl-3-propargyl-methylaminopropane hydrochloride, melting point 165° to 169°C.

1,1-Diphenyl-1-ethoxy-2-methyl-3-(cyclopropylmethyl)-methylaminopropane hydrochloride, melting point 187° to 188°C.

1,1-Diphenyl-1-methoxy-2-methyl-3-(cyclobutylmethyl)-methylaminopropane hydrobromide, melting point 87° to 95°C.

1,1-Diphenyl-1-methoxy-3-benzyl-allylaminopropane hydrochloride, melting point 148° to 151°C.

1,1-Diphenyl-1-ethoxy-3-benzyl-allylaminopropane hydrochloride, melting point 165° to 167°C.

1,1-Diphenyl-1-ethoxy-3-diallylaminopropane hydrochloride, melting point 155° to 156°C.

1,1-Diphenyl-1-propoxy-3-diallylaminopropane hydrochloride, melting point 133° to 137°C.

1,1-Diphenyl-1-methoxy-3-benzyl-(cyclopropylmethyl)-aminopropane hydrochloride, melting point 149° to 152°C.

1,1-Diphenyl-1-ethoxy-3-benzyl-(cyclopropylmethyl)-amino-propane hydrochloride, melting point 165° to 167°C.

1,1-Diphenyl-1-methoxy-2-methyl-3-diallylaminopropane hydrochloride, melting point 160° to 161°C.

1,1-Diphenyl-1-methoxy-3-(cyclobutylmethyl)-ethylaminopropane hydrochloride, melting point 176° to 177°C.

1,1-Diphenyl-1-butoxy-3-allylaminopropane mandelate, melting point 100° to 103°C.

1,1-Diphenyl-1-butoxy-3-crotylaminopropane mandelate, melting point 88° to 91°C.

1,1-Diphenyl-1-butoxy-3-($\gamma,\gamma$-dimethylallyl)-aminopropane mandelate, melting point 121° to 123°C.

1,1-Diphenyl-1-butoxy-3-($\beta$-cyclohexylidene-ethyl)-aminopropane mandelate, melting point 126° to 129°C.

1,1-Diphenyl-1-butoxy-3-(cyclopropylmethyl)-aminopropane mandelate, melting point 114° to 117°C.

1,1-Diphenyl-1-methoxy-2-methyl-3-($\beta$-cyclohexylideneethyl)-aminopropane hydrochloride, melting point 176° to 179°C.

1,1-Diphenyl-1-methoxy-2-methyl-3-($\beta$-cyclohexylideneethyl)-methylaminopropane hydrochloride, melting point 160° to 164°C.

1,1-Diphenyl-1-methoxy-2-methyl-3-(cyclopropylmethyl)-methylaminopropane hydrochloride, melting point 178° to 179°C.

1,1-Diphenyl-1-methoxy-3-(trans-$\gamma$-chloroallyl)-aminopropane hydrochloride, melting point 174° to 176°C.

1,1-Diphenyl-1-methoxy-2-methyl-3-(cyclobutylmethyl)-ethylamino-propane hydrochloride, melting point 128° to 133°C.

1,1-Diphenyl-1-methoxy-2-methyl-3-(cyclobutylmethyl)-methylaminopropane hydrochloride, melting point 151° to 155°C.

The morphine antagonism of the compounds of formula I was tested in the hot plate test on mice. The analgesic properties advantageously can be recognised in chemical pain tests, per example in preventing the "writhing syndrome" caused by i.p. injection of 0.3 ml of a 0.02% phenyl-chinone solution in a mixture of alcohol and water. The analgesic properties are also seen in men. Per example the compound 1,1-diphenyl-1-methoxy-3-allylaminopropane administered in a single dose of 20 mg to healthy test persons in which a well defined pain had been provocated showed a marked analgesic action.

The compounds of formula I can be applicated orally in single doses, of 1 to 30 mg varying with the strength of analgetic effect wanted. The administration may be performed with capsules, which contain the active compound of formula I as bases or as salts. Tablets or dragees can also be made with usual extenders or diluents such as cornstarch, lactose, cellulose, talcum and/or magnesium-stearate. For injection purposes, aqueous solutions can be made from water soluble salts, per example the acetates or lactates of the compounds of formula I.

What we claim is:

1. A member selected from the group consisting of compounds of the formula

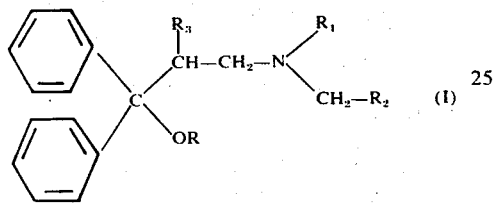

in which R is alkyl with up to four carbon atoms, $R_1$ is selected from the group consisting of hydrogen, alkyl containing up to four carbon atoms and benzyl, $R_2$ is selected from the group consisting of alkenyl containing up to six carbon atoms, aralkenyl, and aralkenyl substituted by a lower alkoxy group, both aralkenyls with the alkenyl group containing up to four carbon atoms, alkinyl containing up to three carbon atoms, cycloalkyl containing up to six carbon atoms and cycloalkylidenemethyl containing up to seven carbon atoms and $R_3$ is selected from the group consisting of hydrogen and methyl, and a salt thereof.

2. A compound according to claim 1, 1,1-Diphenyl-1-methoxy-3-allylamino-propane.

3. A compound according to claim 1, an acid addition salts of 1,1-Diphenyl-1-methoxy-3-allylamino-propane.

4. A compound according to claim 1, 1,1-Diphenyl-1-ethoxy-3-methylallylamino-propane.

5. A compound according to claim 1, 1,1-Diphenyl-1-methoxy-3-(cyclopropylmethyl)-amino-propane.

6. A compound according to claim 1, 1,1-Diphenyl-1-ethoxy-3-allylamino-propane.

7. A compound according to claim 1, 1,1-Diphenyl-1-methoxy-3-methyl-allylamino-propane.

8. A member selected from the group consisting of a compound of the formula

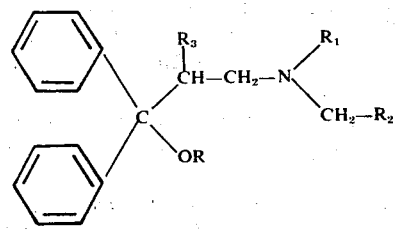

wherein R is alkyl of up to 4 carbon atoms, $R_1$ is hydrogen or alkyl of up to 4 carbon atoms, $R_2$ is alkenyl of up to 6 carbon atoms or cycloalkyl of up to 6 carbon atoms, and $R_3$ is hydrogen or methyl, and a salt thereof.

* * * * *